(12) United States Patent
Van Kesteren

(10) Patent No.: US 8,233,150 B2
(45) Date of Patent: Jul. 31, 2012

(54) SAMPLE CONCENTRATION DETECTOR WITH TEMPERATURE COMPENSATION

(75) Inventor: Hans W. Van Kesteren, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 546 days.

(21) Appl. No.: 12/518,470

(22) PCT Filed: Dec. 10, 2007

(86) PCT No.: PCT/IB2007/054996
§ 371 (c)(1),
(2), (4) Date: Jun. 10, 2009

(87) PCT Pub. No.: WO2008/072167
PCT Pub. Date: Jun. 19, 2008

(65) Prior Publication Data
US 2010/0007889 A1  Jan. 14, 2010

(30) Foreign Application Priority Data
Dec. 12, 2006  (EP) .................................... 06125881

(51) Int. Cl.
G01N 21/00 (2006.01)
G01K 17/00 (2006.01)
(52) U.S. Cl. ........................... 356/436; 356/432; 374/31
(58) Field of Classification Search ........... 356/432–444
See application file for complete search history.

(56) References Cited

U.S. PATENT DOCUMENTS

| | | | | |
|---|---|---|---|---|
| 3,973,852 A | * | 8/1976 | Moore et al. | 356/438 |
| 4,725,148 A | * | 2/1988 | Endo et al. | 356/442 |
| 4,968,887 A | * | 11/1990 | Wong | 250/343 |
| 5,047,639 A | * | 9/1991 | Wong | 250/341.1 |
| 5,243,983 A | * | 9/1993 | Tarr et al. | 600/318 |
| 5,267,019 A | * | 11/1993 | Whittaker et al. | 356/437 |
| 5,625,189 A | * | 4/1997 | McCaul et al. | 250/343 |

(Continued)

FOREIGN PATENT DOCUMENTS

DE  19516974 A1  10/1996

(Continued)

OTHER PUBLICATIONS

Wahr, J. A., et al.; Near-Infrared Spectroscopy: Theory and Applications; 1996; J. of Cardiothoracic and Vascular Anesthesia; 10(3)406-418.

*Primary Examiner* — Gregory J Toatley
*Assistant Examiner* — Jarreas C Underwood

(57) ABSTRACT

A sample sensor (200) for detecting a concentration of a sample in a sample mixture, the sample sensor (200) comprising a light source (101), a detector element, a processing section (106) and parameter measuring means. The light source (101) produces a light beam (113) for exciting molecules of the sample. The detector element detects an 5 amount of excited molecules of the sample and provides a detector current indicating the amount. The processing section (106) is coupled to the detector element (103) for processing the detector current to generate an output signal (109) representing the concentration. The processing section (106) comprises a temperature compensation module (112) being arranged for compensating for a temperature dependent wavelength shift of the light source (101) 10 based on at least one measured value of a temperature dependent parameter of the light source (101), other than an output wavelength. The parameter measuring means obtain the at least one measured value.

18 Claims, 6 Drawing Sheets

U.S. PATENT DOCUMENTS

| | | | |
|---|---|---|---|
| 5,638,816 A * | 6/1997 | Kiani-Azarbayjany et al. | 600/316 |
| 6,552,792 B1 | 4/2003 | Pilgrim et al. | |
| 7,599,807 B2 * | 10/2009 | Tombs | 702/45 |
| 2003/0020030 A1 * | 1/2003 | Harada et al. | 250/573 |
| 2006/0263256 A1 | 11/2006 | Koshel et al. | |

FOREIGN PATENT DOCUMENTS

| | | |
|---|---|---|
| DE | 10308409 A1 | 9/2004 |
| EP | 1111370 A1 | 6/2001 |
| GB | 2286458 A | 8/1995 |
| GB | 2353591 A | 2/2001 |
| JP | 09192120 A | 7/1997 |
| WO | 9218847 A1 | 10/1992 |
| WO | 9829733 A1 | 7/1998 |
| WO | 2004023114 A1 | 3/2004 |

* cited by examiner

SAMPLE CONCENTRATION DETECTOR WITH TEMPERATURE COMPENSATION

TECHNICAL FIELD OF THE INVENTION

The invention relates to a sample sensor for detecting a concentration of a sample in a sample mixture, the sample sensor comprising a light source for producing a light beam for exciting molecules of the sample, a detector element for detecting an amount of excited molecules of the sample and providing a detector current indicating the amount and a processing section, coupled to the detector element for processing the detector current to generate an output signal representing the concentration, the sample sensor further comprising means for compensating for a temperature dependent wavelength shift of the light source.

BACKGROUND OF THE INVENTION

Such a sample sensor is known from U.S. Pat. No. 6,552,792. This US patent describes a wavelength modulated photo acoustic spectrometry system and method for measuring a concentration of a trace gas in a gas mixture. The method comprises generating light from a light source; passing the light through a sample area; sampling sound produced by the light passing through the sample area with an acoustic detector; and controlling the wavelength of the light with a wavelength controller. The wavelength modulation is performed with a frequency f, around the optimal absorption wavelength of the trace gas. When, due to temperature variation, the average wavelength of the light from the light source changes, the wavelength shift is detected. A wavelength controller compensates for this effect by adjusting the average wavelength.

The temperature compensation is performed as follows. Part of the light passes through a reference gas cell with a relatively high concentration of the trace gas. A photo diode behind the reference cell provides a signal that depends on the absorption in the reference cell. The wavelength modulation with a frequency f results in variations in the photo diode signal with a frequency 2f (two absorption peaks for every modulation period). When, due to a temperature change, the wavelength of the light produced by the light source is shifted, the modulation is not performed exactly around the optimal absorption value anymore. As a result, odd harmonics (3f) of the modulation frequency are introduced in the detector signal. The 3f signal on the photo detector varies when the average wavelength shifts through the absorption spectrum of the trace gas and equals zero when the average laser wavelength corresponds to the centre of the absorption line. The wavelength controller adjusts the average wavelength of the light source in order to minimize the 3f component in the photo diode signal.

Although this approach can be used for fundamental studies in research institutes, the use of a reference gas cell is not a preferred approach for a commercial product. Because the reference gas cell signal is based on absorption, a long reference gas cell is required which is not attractive for a compact sensor or a high concentration needs to be used which in case of, for example, $NO_2$ becomes dangerous when the reference gas cell accidentally breaks. Furthermore it is a problem of the reference gas cell, that the concentration of some gases is not stable over long periods due to for instance wall sticking or dissociation.

SUMMARY OF THE INVENTION

It is an object of the invention to provide a sample sensor capable of correcting the output signal for temperature variations, without using a reference gas cell.

According to a first aspect of the invention, this object is achieved by providing a sample sensor according to the opening paragraph, wherein the processing section comprising a temperature compensation module being arranged for compensating for the temperature dependent wavelength shift of the light source based on at least one measured value of a temperature dependent parameter of the light source, other than an output wavelength, and wherein the sample sensor further comprises parameter measuring means for obtaining the at least one measured value.

The invention is based on the idea that not only the wavelength of the emitted light depends on the temperature, but also other light source parameters are temperature dependent and that said dependencies may be used for compensating for the temperature dependent wavelength shift of the light source. The at least one measured value is obtained by the parameter measuring means. The value of the light source parameter is a direct consequence of the temperature and the temperature is determinative for the output wavelength of the light source. Consequently, the required temperature compensation is derivable from the measured parameter of the light source. The sample sensor according to the invention is suited for temperature compensation, but does not require a reference gas cell for determining the temperature dependent wavelength shift.

Variations in temperature are related to variations in the wavelength of the light emitted by the light source. The variations in the wavelength correspond to deviations in the detector current. These relations are used for compensating for the temperature dependent wavelength shift based on the at least one measured value.

In an embodiment the sample sensor is a photo acoustic detector and comprises a light modulator for modulating the light beam for varying the amount of excited molecules and thereby generating pressure variations in the sample mixture, and the detector element comprises a pressure sensor for converting the pressure variations into the detector current.

In another embodiment the detection is based on optical absorption of the light beam by the sample and the sample sensor comprises a photodiode for measuring optical absorption caused by the exciting of the molecules of the sample, and for converting the optical absorption into the detector current.

In an embodiment, the sample sensor further comprises wavelength adjustment means, coupled to the temperature compensation module, for performing the compensating by controlling the output wavelength.

The temperature dependent wavelength shift is then compensated for by, after the calculation of the wavelength shift, adjusting the output wavelength of the light source such that the wavelength shift is compensated.

In another embodiment, the temperature compensation means are arranged for performing the compensating by correcting the output signal for the temperature dependent wavelength shift.

In contrast with the previous embodiment and the system of U.S. Pat. No. 6,552,792, the sample sensor according to this embodiment does not prevent temperature dependent wavelength shifts, but instead accepts the wavelength shifts and corrects the output signal based on the at least one measured value of another temperature dependent parameter of the light source.

The at least one measured value may be an optical output power of the light source and the parameter measuring means then comprise an internal photodiode for direct measurement of the optical output power.

Direct measurement of the laser power is much easier than measuring absorption by a reference gas in a reference cell.

Alternatively or additionally, the light source is a semiconductor laser diode and the at least one measured value is a threshold forward current through the semiconductor laser diode, beneath which threshold current the optical output power is substantially zero and above which threshold current the optical output power substantially increases. In another embodiment of a sample sensor with a semiconductor laser diode the at least one measured value is a forward voltage of the semiconductor laser diode.

It is seen for semiconductor lasers that the threshold current and output power at fixed current change in a well-defined way as a function of laser temperature. Also the voltage changes in a well defined way at a fixed current. So by determining the threshold current, the power, or the laser voltage at a certain laser current the temperature can be derived. The wavelength (change) and related absorption change can now easily be obtained from the (known or earlier measured) wavelength versus temperature dependence and the absorption spectrum.

Alternatively, the temperature compensation module uses a calibration factor from a calibration measurement wherein the optical output power and the detector current have been measured at various temperatures, using a known calibration concentration of the sample and a known calibration driving current for the light source.

According to a second aspect of the invention, a method is provided for determining the calibration factor for temperature compensation of the output signal in a photo acoustic detector as described in the previous paragraph, the method comprising measuring the optical output power and the detector current at various temperatures while using a known calibration concentration of the sample and a known calibration driving current for the light source, and determining the calibration factor from the measured optical output powers and the measured detector currents.

Alternatively, the calibration factor is related to the forward voltage of a semiconductor laser instead of to its optical output power.

According to another aspect of the invention, a method is provided for correcting the output signal of a photo acoustic detector according to the invention for a temperature dependent wavelength shift of the light source, the method comprising measuring at least one value of another temperature dependent parameter of the light source, and correcting the output signal based on the measured at least one value.

These and other aspects of the invention are apparent from and will be elucidated with reference to the embodiments described hereinafter.

DETAILED DESCRIPTION OF THE INVENTION

Figure 1:
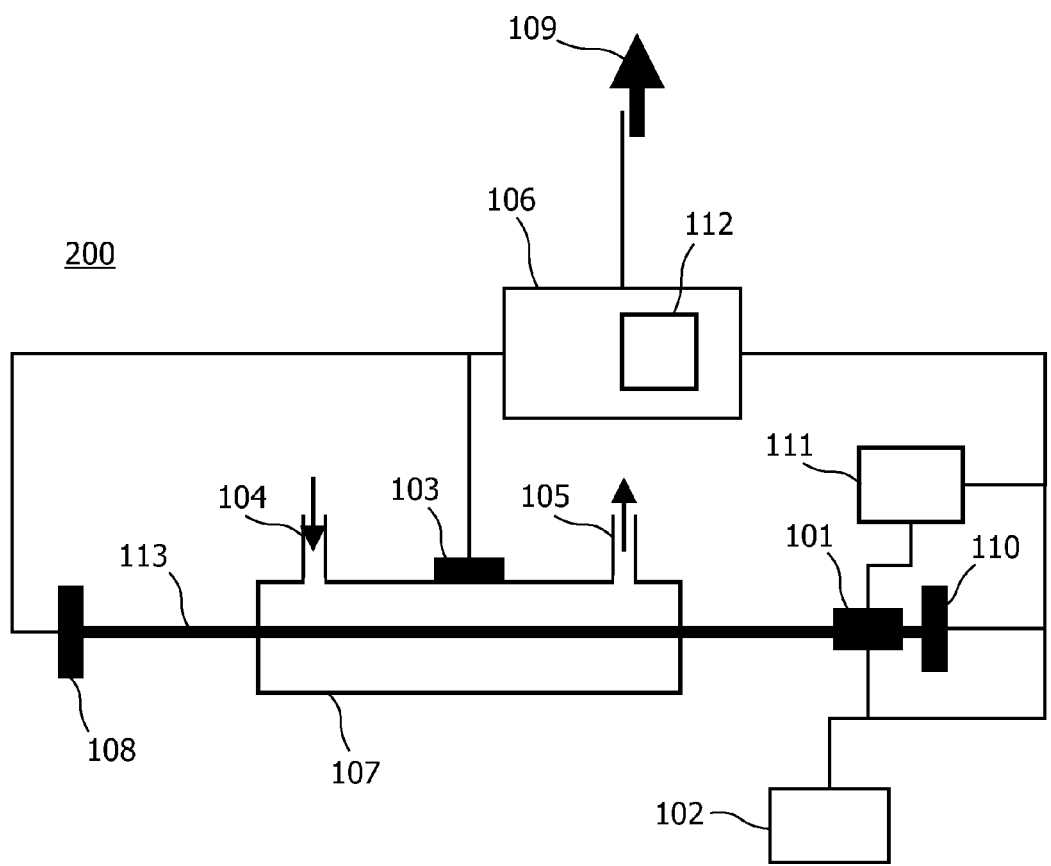
FIG. 1 schematically shows an embodiment of the photo acoustic detector according to the invention.

FIG. 1 schematically shows an embodiment of the sample sensor 200 according to the invention. The sample sensor 200, shown in FIG. 1 is a photo acoustic detector, which is also arranged for detecting sample concentrations based on optical absorption. The description below primarily describes the photo acoustic detector, but a skilled person could easily understand that the temperature compensation works in the same way when using optical absorption for measuring the concentration. Optionally, both techniques are used in parallel for obtaining more reliable measurements.

The photo acoustic trace gas detector 200 described hereinafter detects trace gas concentrations in a gas mixture, but the invention may also be applied to detect tissue, fluid or solid samples in other sample mixtures. The gas mixture to be tested is comprised in the gas cell 107. The gas cell 107 may comprise a gas inlet 104 and a gas outlet 105 for filling and emptying the gas cell 107. In an apparatus for breath testing, a user may blow air to be tested through the gas cell 107.

The trace gas detector 200 uses a laser diode 101 as a light source. The wavelength of the laser light 113 is chosen such that it can excite the trace gas molecules. Alternatively, other types of laser sources or other light sources, capable of producing a light beam with sufficient energy to excite the trace gas molecules may be used. A laser driver 102 provides a driving signal for the laser diode 101. In this embodiment, the laser driver 102 also functions as a modulator for modulating the light beam. By varying the current provided by the laser driver 102, the intensity of the light beam 113 is varied over time. Modulation of the intensity of the light beam may also be realized by manipulating a light beam with a continuous intensity. It is, for example, known to us a mechanical chopper for generating an intensity modulated light beam from a continuous wave light beam.

A higher intensity of the laser beam 113 results in more molecules in the trace gas being excited, which leads to a higher temperature of the gas mixture. A larger amplitude of the driving signal results in more excitations and larger temperature fluctuations. A higher concentration of the trace gas, via increased excitation of trace gas molecules, also results in larger temperature fluctuations. The temperature fluctuations cause pressure variations or sound waves in the gas mixture. The pressure variations are detected by a detector element 103, such as a microphone or an oscillator element. If the laser light is modulated at the resonance frequency of an oscillator element, the sound waves excite the oscillator. Preferably, the oscillator element is a crystal oscillator, such as a quartz tuning fork. Quartz tuning forks have a high sensitivity and operate at a high frequency. Furthermore, quartz tuning forks are not very expensive because they are used on large scale, for example, for the manufacturing of digital watches.

The signal from the detector 103 is sent to a processing section 106 for generating an output signal 109 representing the concentration of the trace gas. According to the invention, some parameters of the light source are measured by parameter measuring means 111 and the parameters are also provided to the processing section 106. For example, the driving current through the laser diode 101 or the forward voltage over the laser diode 101 are sent to the processing section 106. The forward current may also directly be obtained from the laser driver 102. Another parameter that may be provided to the processing section 106 is the output power of the light source 101. In this embodiment, the output power is measured by an internal photodiode 110, placed directly behind the rear facet of the laser diode 101. As will be elucidated hereinafter, these light source parameters are used by a temperature compensation module 112 of the processing section 106 for compensating for temperature dependent wavelength shifts. As these parameters are directly obtainable from the light source 101, the temperature compensation is much easier than in the prior art photo acoustic detector described above, which required a reference gas cell with a reference gas.

A photo diode 108 is placed at the position where the light beam leaves the gas cell. This photo diode 108 is used for measuring the concentration based on optical absorption. A difference of the photo diode signal when measuring with or without the sample being present in the gas cell is then used as input for the processing unit.

Figure 2A:
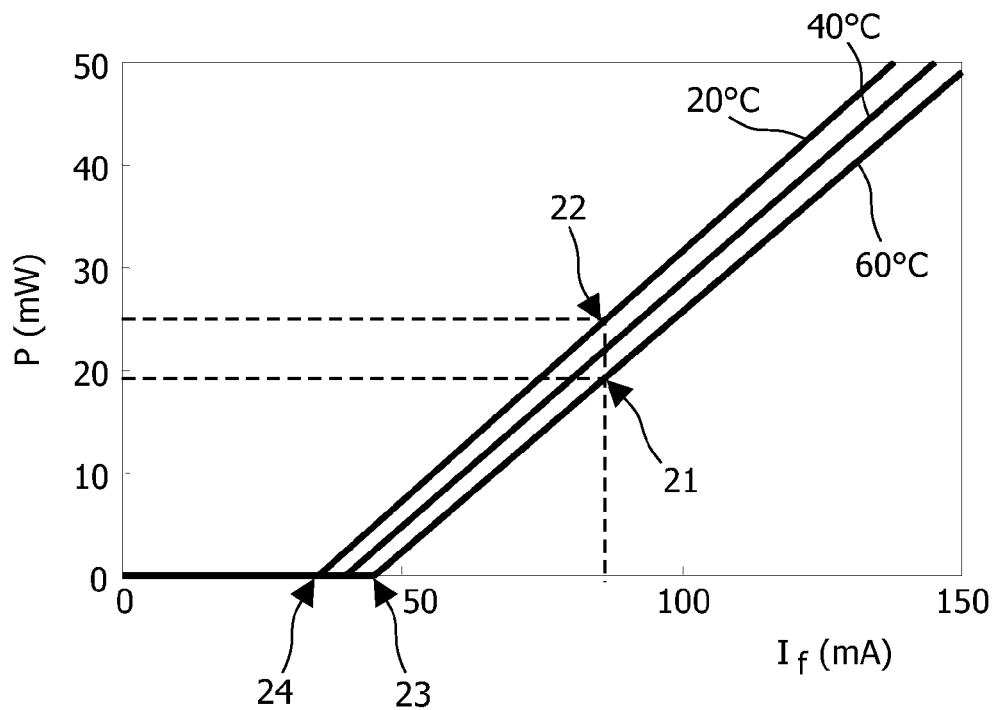
FIG. 2a shows a relation between a forward current through a laser diode and an output power of the laser diode at different temperatures.

FIG. 2a shows a relation between a forward current through a laser diode 101 and an output power of the laser diode 101 at different temperatures (20° C., 40° C. and 60°). At all temperatures low forward currents, $I_f$, do not result in any laser output power, $P_{out}$. When $I_f$ is above a threshold current, $I_{th}$, the laser diode starts to emit light. The threshold current, $I_{th}$, depends on the temperature of the laser diode. As can be seen in FIG. 2a, at low temperatures (20° C.), $I_{th}$ 24 is smaller than $I_{th}$ 23 at higher temperatures (60° C.). Thus, if $I_{th}$ is known for different temperatures, the laser diode temperature can be determined by determining $I_{th}$. Usually the relation between $I_{th}$ and temperature is provided by the supplier of the laser diode. If not, the relation may be obtained via a calibration measurement. Alternatively or additionally, the diode temperature may also be determined by measuring $P_{out}$ for a known forward current, which is preferably larger than $I_{th}$ for the highest possible temperatures. As can be seen in FIG. 2a, at a fixed forward current, $P_{out}$ 22 is larger at low temperatures (20° C.) than $P_{out}$ 21 at higher temperatures (60° C.). The relation between $P_{out}$ and temperature for a predetermined forward current may also be provided by the supplier of the laser diode or obtained via a calibration measurement.

Figure 2B:
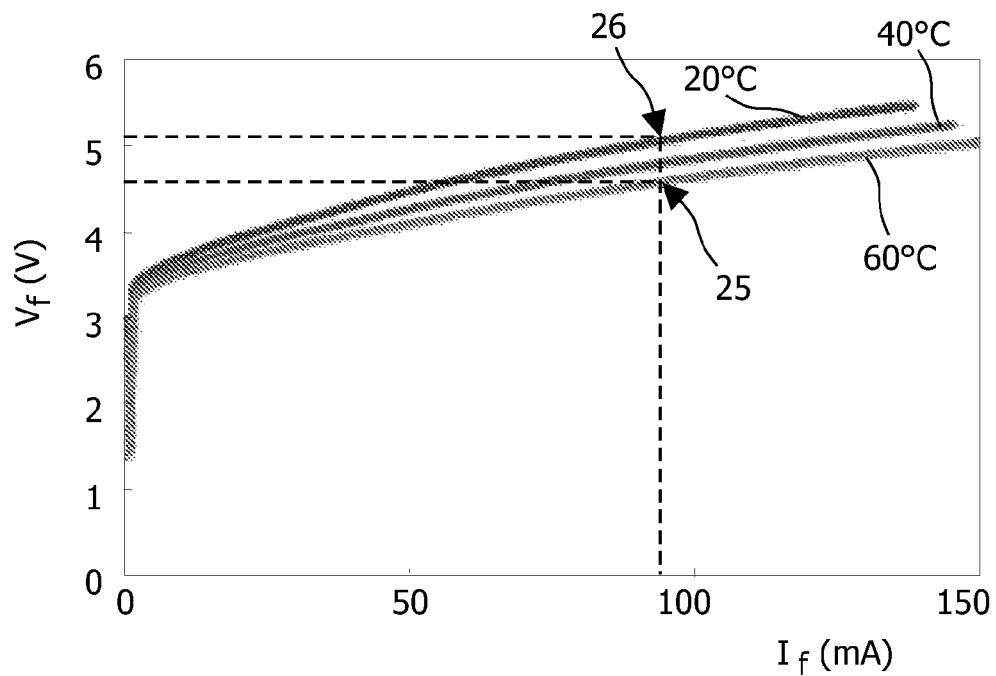
FIG. 2b shows a relation between a forward current through a laser diode and a forward voltage over the laser diode at different temperatures.

FIG. 2b shows a relation between a forward current through a laser diode and a forward voltage, $V_f$, over the laser diode at different temperatures. As can be seen in FIG. 2b, at a fixed forward current, $V_f$ 26 is larger at low temperatures (20° C.) than $V_f$ 25 at higher temperatures (60° C.). The relation between $V_f$ and temperature for a predetermined forward current may also be provided by the supplier of the laser diode or obtained via a calibration measurement.

Figure 3:
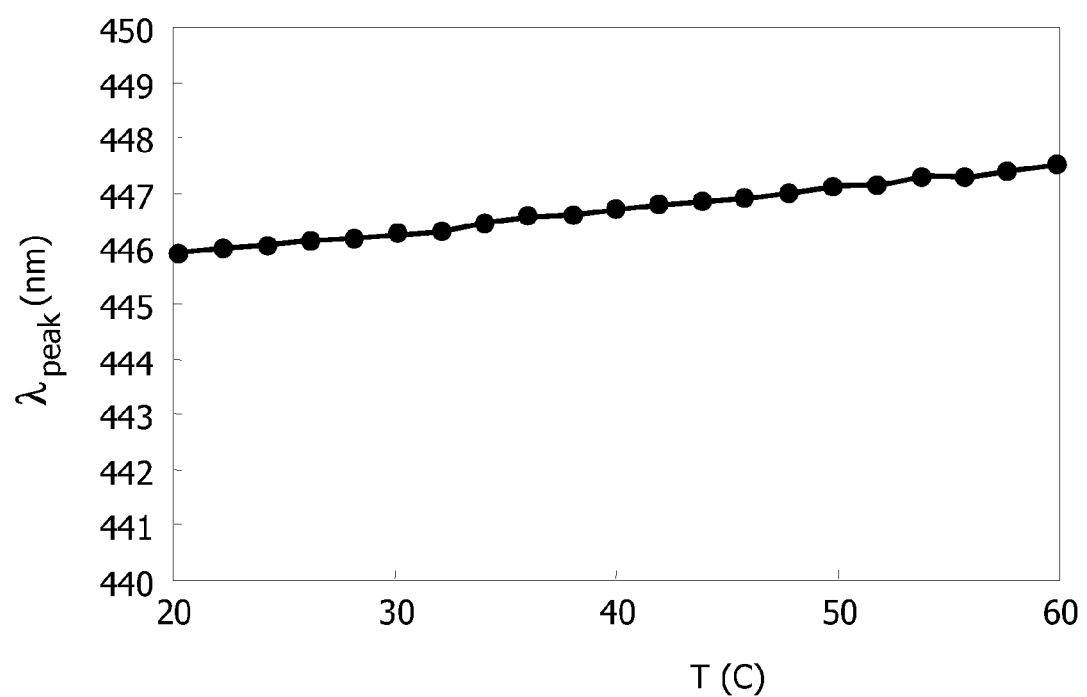
FIG. 3 shows a relation between the temperature and a peak wavelength of a laser diode.

FIG. 3 shows a relation between the temperature and a peak wavelength, $\lambda_{peak}$, of a laser diode. After the determination of the laser diode temperature using the information from FIG. 2a or FIG. 2b, the temperature dependent wavelength shift of the laser diode is determined using the information from FIG. 3. Depending on the absorption spectrum of the sample, this wavelength shift has a small or large effect on the absorption of the light by the sample molecules. The temperature compensation module 112 of the processing section 106 may then adjust the average output wavelength of the light or may apply a correction to the output signal 109. Adapting the output wavelength of the light source 101 may be done in several ways as commonly known in the art. The correction of the output signal 109 is performed by determining the contribution of the wavelength shift to the original non-corrected output signal 109. This contribution is calculated using, amongst others, the measured value of the temperature dependent parameter of the light source 101, other than the output wavelength.

Figure 4A:
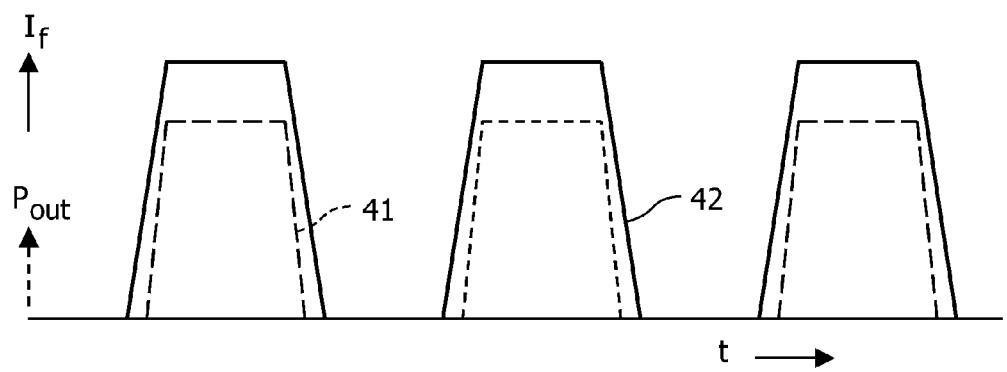
FIG. 4a shows an exemplary waveform for the forward current through the light source and of the output power waveform resulting there from, FIG. 4b is a zoomed view of a part of the waveforms of FIG. 4a, FIGS. 5, 6 and 7 show results of a calibration method according to the invention.

FIG. 4a shows an exemplary waveform for the forward current 42, $I_f$, through the light source (solid line) and for the optical output power 41, $P_{out}$ (dotted line) resulting there from. With the modulation scheme shown in FIG. 4a, two different temperature dependent parameters of the laser diode can be obtained. How these parameters are obtained is elucidated with reference to FIG. 4b.

Figure 4B:
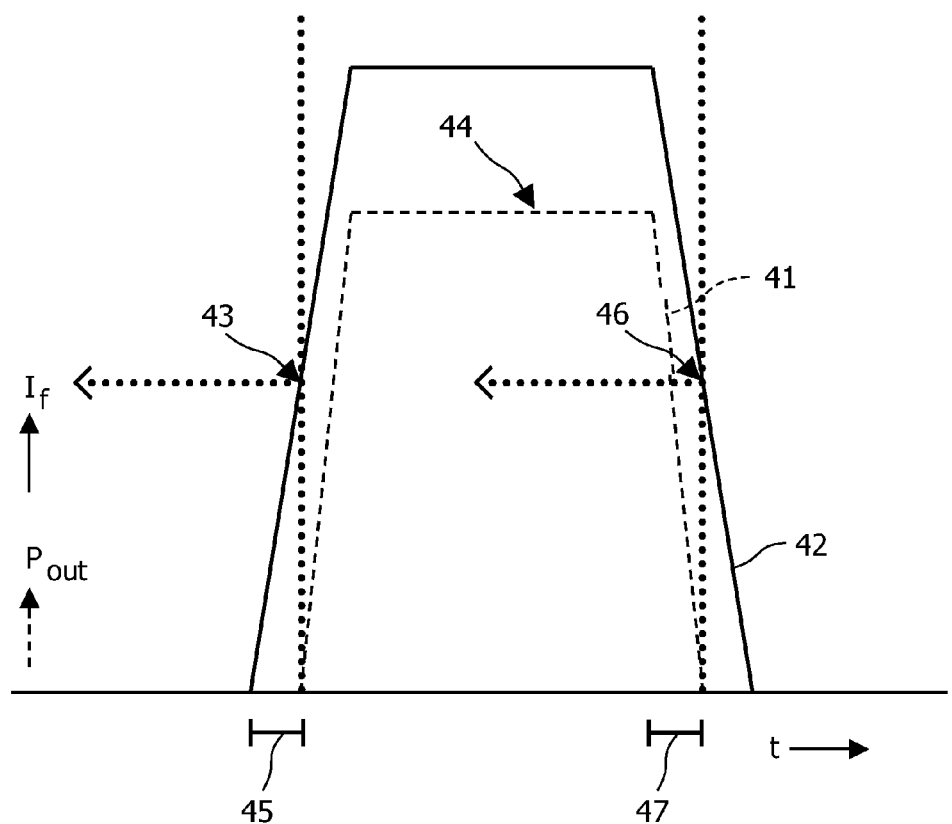

FIG. 4b is a zoomed view of a part of the waveforms of FIG. 4a. As described above with reference to FIG. 2a, the temperature of the laser diode may be determined using the threshold current, $I_{th}$, or the optical output power, $P_{out}$, at a predetermined forward current, $I_f$. These two temperature dependent parameters may be obtained from the waveform signals 41, 42 shown in FIG. 4b. $I_{th}$ is the value for $I_f$ at the moment 43 that $P_{out}$ starts increasing or at the moment 46 that $P_{out}$ reaches it minimum value. If the shape of the $I_f$ waveform 42 is known, the $I_{th}$ may also be obtained from the time delay 45 from the moment $I_f$ starts increasing until the moment that the $P_{out}$ also starts increasing. This method is quite useful because $I_f$ is controlled by the laser driver 102 and the shape of the $I_f$ waveform 42 is therefore known. An equal time delay occurs between the moments that $P_{out}$ and $I_f$ reach their respective minimum values. When $I_{th}$ is known, the temperature of the laser diode 101 is determined using the information in FIG. 2a.

The temperature may alternatively or additionally be obtained from the optical output power, $P_{out}$, at a predetermined forward current, $I_f$. In principle this may be done at any $I_f$ within the amplitude of the driving current modulation. Preferably, the temperature of the laser diode 101 is determined based on $P_{out}$ at the predetermined maximum value for $I_f$. This value 44 for $P_{out}$ is the maximum value of $P_{out}$ during the modulation. Knowing the maximum values of $I_f$ and $P_{out}$, the temperature of the laser diode 101 is determined using the information in FIG. 2a. Alternatively, the forward voltage $V_f$ may be measured while modulation the forward current, $I_f$. Knowing the maximum (or other corresponding) values of $I_f$ and $V_f$, the temperature of the laser diode 101 is then determined using the information in FIG. 2b.

Figure 5:
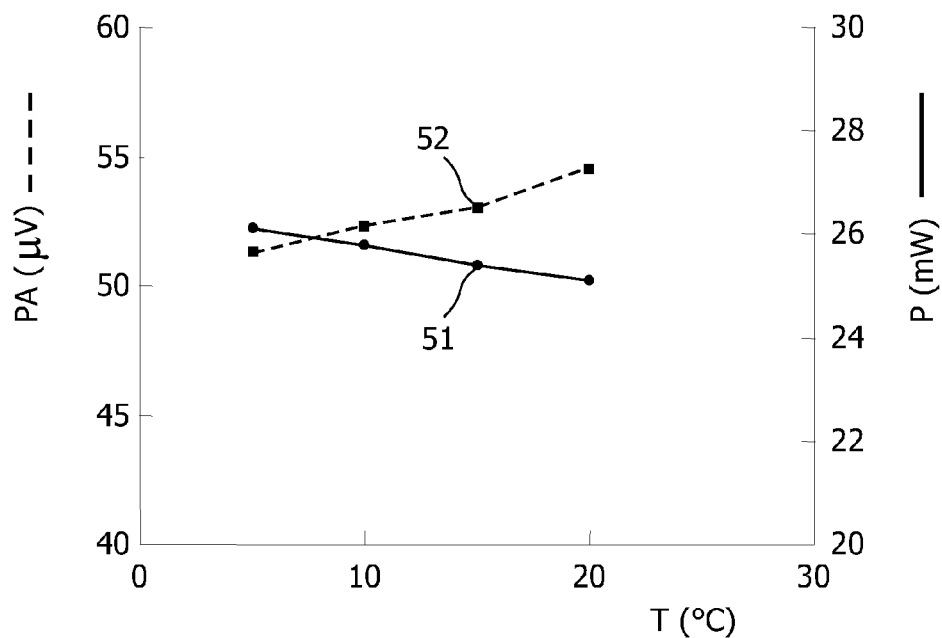
Figure 6:
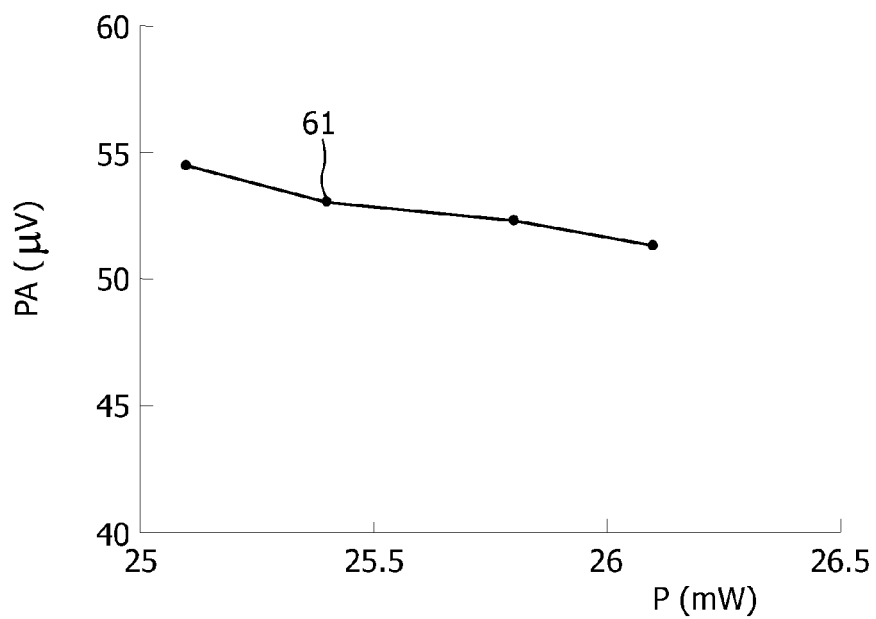
Figure 7:
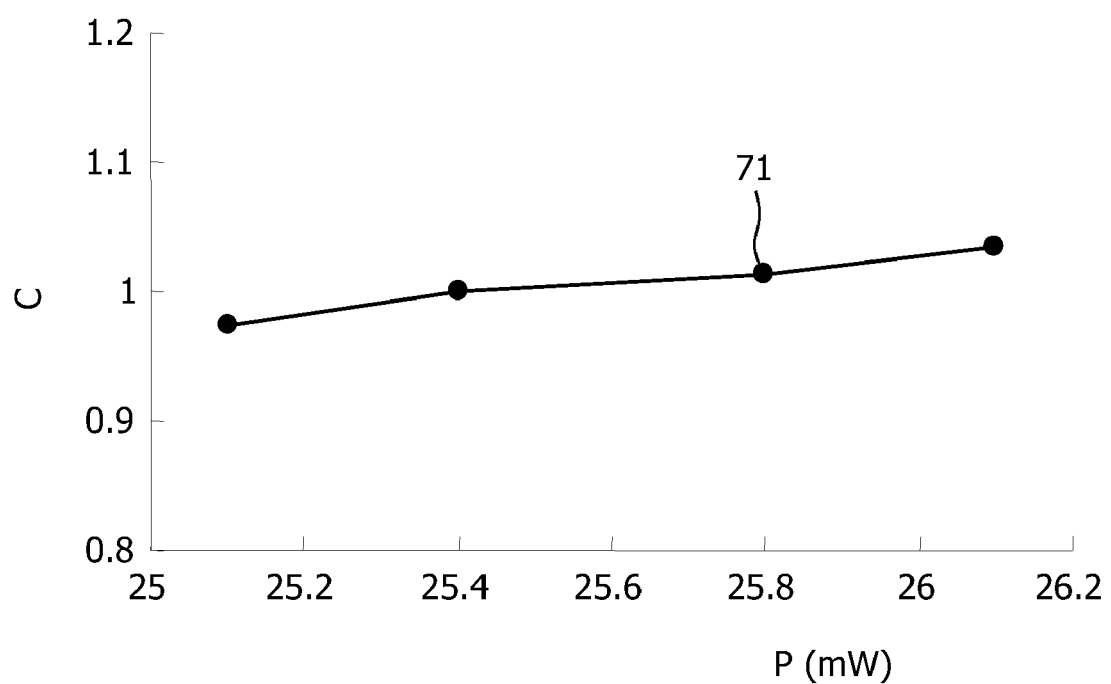

FIGS. 5, 6 and 7 show results of a temperature compensation calibration method according to the invention. In this calibration measurement the laser diode 101 housing was placed on a Peltier element to control its temperature. FIG. 5 shows the measured power 51 (solid line) determined from the response of the internal photodiode 110 and the output signal 52 (dotted line), both as a function of the temperature of the laser housing. During the calibration measurement the concentration of the sample in the sample mixture led through or kept in the cell 107 and the forward current modulation amplitude of the diode laser 101 are both fixed. A reduction in temperature leads to an increase in laser output power, $P_{out}$ 51, but a decrease of the photo acoustic output signal 52, which is due to the wavelength shift of the light source 101 and the shape (fine-structure) of the sample absorption spectrum. From the power and output signal 52 versus temperature dependencies a temperature compensation calibration curve 61 can be obtained which is shown in FIG. 6. The calibration curve 61 shows the relation between the output power measured by the internal photodiode 110 and the photo acoustic detector signal. For making it possible to measure unknown gas concentrations with a photo acoustic gas cell without control of the temperature of the laser diode a concentration calibration is carried out. For this a known sample concentration [$S_{ref}$] is applied to the gas cell and the same current modulation amplitude during the temperature compensation calibration is applied. Subsequently, the photo acoustic signal $PA_{ref}$ is determined as well as the signal $P_{ref}$ on the internal photo diode 110. A temperature compensation curve as shown in FIG. 7 is then derived from the calibration curve 61 by normalizing the photo acoustic signal to 1 at $P=P_{ref}$.

Using FIG. 7, an unknown sample concentration may be determined by applying the same forward current modulation amplitude to the laser diode as during the calibration measurement, measuring the output signal and correcting the measured output signal using the following formula:

$$[S] = [S]_{ref} * \frac{PA}{PA_{ref}} * C(P),$$

wherein [S] is the concentration of the sample, $[S]_{ref}$ is the known calibration concentration, PA is the output signal, $PA_{ref}$ is the output signal during the concentration calibration measurement and C(P) is the temperature compensation factor for the optical output power during the measurement of the unknown sample concentration. During the concentration calibration measurement the sample concentration is $[S]_{ref}$ and the optical power measured by the internal photo diode is $P_{ref}$.

The calibration method described above, with reference to FIGS. 5, 6 and 7, may also be performed using another temperature dependent parameter of the light source 101. For example, the forward voltage, $V_f$, over a laser diode 101 may be measured instead of the output power, $P_{out}$.

The temperature compensation factor C(P) or $C(V_f)$ can be implemented for instance in the form of a look-up table in the temperature compensation module 112. The temperature compensation curve itself can be obtained in a number of ways. In the temperature compensation calibration routine described above an experimental approach is taken. Another method to derive the temperature compensation curve is to determine the temperature dependence of wavelength and output power either or not in combination with the reverse voltage of the laser diode and to combine these with a high resolution absorption line-shape of the sample gas. When sensors have to be produced in high-volumes and lasers are applied with variation in initial wavelength it might be appropriate to determine temperature compensation curves for lasers within a set of initial wavelengths and select the appropriate compensation curve for a certain sensor module by determining only the peak wavelength for the laser and selecting the right compensation curve from a database.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the claims enumerating several means, several of these means may be embodied by one and the same item of hardware. The mere fact that certain measures are recited in mutually different dependent claims does not indicate that a combination of these measures cannot be used to advantage.

The invention claimed is:

1. A sample sensor for detecting a concentration of a sample in a sample mixture, the sample sensor comprising:
a light source for producing a light beam for exciting molecules of the sample,
a detector element for detecting an amount of excited molecules of the sample and providing a detector current indicating the amount,
a processing section, coupled to the detector element for processing the detector current to generate an output signal representing the concentration, the processing section comprising a temperature compensation module being arranged for compensating for a temperature dependent wavelength shift of the light source based on at least one measured value of a temperature dependent parameter of the light source, other than an output wavelength, and
parameter measuring means for obtaining the at least one measured value, and
wavelength adjustment means coupled to the temperature compensation module for performing the compensating by controlling the output wavelength.

2. A sample sensor according to claim 1, further comprising a light modulator for modulating the light beam for varying the amount of excited molecules and thereby generating pressure variations in the sample mixture, and wherein the detector element comprises a pressure sensor for converting the pressure variations into the detector current.

3. A sample sensor according to claim 1, wherein the detector element comprises a photodiode for measuring optical absorption caused by the exciting of the molecules of the sample, and for converting the optical absorption into the detector current.

4. A sample sensor according to claim 1, wherein the temperature compensation means are arranged for performing the compensating by correcting the output signal for the temperature dependent wavelength shift.

5. A sample sensor according to claim 1, wherein the at least one measured value is an optical output power of the light source and wherein the parameter measuring means comprise an internal photodiode for direct measurement of the optical output power.

6. A sample sensor according to claim 1, wherein the light source is a semiconductor laser diode and the at least one measured value is a threshold forward current through the semiconductor laser diode, beneath which threshold current the optical output power is substantially zero and above which threshold current the optical output power substantially increases.

7. A sample sensor according to claim 1, wherein the light source is a semiconductor laser diode and the at least one measured value is a forward voltage of the semiconductor laser diode.

8. A sample sensor according to claim 1, wherein the temperature compensation module uses a calibration factor from a calibration measurement wherein the optical output power and the detector current have been measured at various temperatures, using a known calibration concentration of the sample and a known calibration driving current for the light source.

9. A sample sensor according to claim 6, wherein the temperature compensation module uses the following formula:

$$[S] = [S]_{ref} * \frac{PA}{PA_{ref}} * C(P),$$

wherein [S] is the concentration of the sample, $[S]_{ref}$ is the known calibration concentration, PA is the detector current, $PA_{ref}$ is a detector current during the calibration measurement and C(P) is a calibration factor corresponding to the optical output power, P, during the sample measurement, $PA_{ref}$ being derived from the calibration measurement.

10. A sample sensor according to claim 4, wherein the temperature compensation module uses a calibration factor from a calibration measurement wherein the forward voltage and the detector current have been measured at various temperatures, using a known calibration concentration of the sample and a known calibration driving current for the light source.

11. A sample sensor according to claim 8, wherein the temperature compensation module uses the following formula:

$$[S] = [S]_{ref} * \frac{PA}{PA_{ref}} * C(V_f),$$

wherein [S] is the concentration of the sample, $[S]_{ref}$ is the known calibration concentration, PA is the detector current, $PA_{ref}(V_f)$ is a detector current during the calibration measurement corresponding to the forward voltage, $V_f$, and $C(V_f)$ is a calibration factor corresponding to the forward voltage, $V_f$, $PA_{ref}(V_f)$ and $C(V_f)$ being derived from the calibration measurement.

12. A method for determining the calibration factor for temperature compensation of the output signal in a sample sensor, the method comprising:

producing, by a light source, a light beam for exciting molecules of the sample, detecting, by a detector element, an amount of excited molecules of the sample and providing a detector current indicating the amount, processing, by a processing section coupled to the detector element, the detector current to generate an output signal representing the concentration, the processing section comprising a temperature compensation module;

compensating, by the temperature compensating module, for a temperature dependent wavelength shift of the light source based on at least one measured value of a temperature dependent parameter of the light source, other than an output wavelength, wherein a wavelength adjustment means coupled to the temperature compensation module for performing the compensating by controlling the output wavelength obtaining, by parameter measuring means, the at least one measured value, measuring the optical output power and the detector current at various temperatures while using a known calibration concentration of the sample and a known calibration driving current for the light source, and from the measured optical output powers and the measured detector currents, determining the calibration factor, wherein the temperature compensation means are arranged for performing the compensating by correcting the output signal for the temperature dependent wavelength shift.

13. A method for determining the calibration factor for temperature compensation of the output signal in a sample sensor, the method comprising:

producing, by a light source, a light beam for exciting molecules of the sample, detecting, by a detector element, an amount of excited molecules of the sample and providing a detector current indicating the amount, processing, by a processing section coupled to the detector element, the detector current to generate an output signal representing the concentration, the processing section comprising a temperature compensation module;

compensating, by the temperature compensating module, for a temperature dependent wavelength shift of the light source based on at least one measured value of a temperature dependent parameter of the light source, other than an output wavelength, wherein a wavelength adjustment means coupled to the temperature compensation module for performing the compensating by controlling the output wavelength obtaining, by parameter measuring means, the at least one measured value, measuring the forward voltage and the detector current at various temperatures while using a known calibration concentration of the sample and a known calibration driving current for the light source, and from the measured forward voltages and the measured detector currents, determining the calibration factor, wherein the light source is a semiconductor laser diode and the at least one measured value is a threshold forward current through the semiconductor laser diode, beneath which threshold current the optical output power is substantially zero and above which threshold current the optical output power substantially increases.

14. A method for correcting the output signal of a sample sensor for a temperature dependent wavelength shift of the light source, the method comprising:

producing, by a light source, a light beam for exciting molecules of the sample, detecting, by a detector element, an amount of excited molecules of the sample and providing a detector current indicating the amount, processing, by a processing section coupled to the detector element, the detector current to generate an output signal representing the concentration, the processing section comprising a temperature compensation module;

compensating, by the temperature compensating module, for a temperature dependent wavelength shift of the light source based on at least one measured value of a temperature dependent parameter of the light source, other than an output wavelength, wherein a wavelength adjustment means coupled to the temperature compensation module for performing the compensating by controlling the output wavelength obtaining, by parameter measuring means, the at least one measured value, measuring at least one value of another temperature dependent parameter of the light source, and correcting the output signal based on the measured at least one value.

15. A method according to claim 12, wherein the at least one value is an optical output power of the light beam.

16. A method according to claim 13, wherein the light source is a semiconductor laser diode and the at least one measured value is a threshold forward current through the semiconductor laser diode, beneath which threshold current the optical output power is substantially zero and above which threshold current the optical output power substantially increases.

17. A method according to claim 12, wherein the at least one value is a forward voltage of the light source.

18. A method according to claim 12, wherein the correcting comprises using a calibration factor, obtained by the temperature compensation module, from a calibration measurement, and wherein the forward voltage and the detector current have been measured at various temperatures, using a known calibration concentration of the sample and a known calibration driving current for the light source.

* * * * *